United States Patent [19]
Eagles et al.

[11] Patent Number: 5,893,837
[45] Date of Patent: Apr. 13, 1999

[54] GLAUCOMA DRAIN IMPLANTING DEVICE AND METHOD

[75] Inventors: Daniel C. Eagles, Studio City; Vladimir Feingold, Laguna Niguel, both of Calif.

[73] Assignee: Staar Surgical Company, Inc., Monrovia, Calif.

[21] Appl. No.: 08/808,577

[22] Filed: Feb. 28, 1997

[51] Int. Cl.⁶ .................................................. A61M 5/00
[52] U.S. Cl. ................... 604/9; 604/264; 604/294; 606/108
[58] Field of Search .................... 604/8–10, 28, 604/22, 49, 51, 104, 164, 175, 264, 272, 274, 280, 294; 606/108–109

[56] References Cited

U.S. PATENT DOCUMENTS

| | | | |
|---|---|---|---|
| 5,037,384 | 8/1991 | Chang | 604/28 |
| 5,092,837 | 3/1992 | Ritch et al. | 604/8 |
| 5,360,425 | 11/1994 | Cho | 606/6 |
| 5,364,374 | 11/1994 | Morrison et al. | 604/272 |
| 5,656,026 | 8/1997 | Joseph | 604/9 |
| 5,683,408 | 11/1997 | De Laage De Meux et al. | 606/184 |

*Primary Examiner*—John G. Weiss
*Assistant Examiner*—Ki Yong O
*Attorney, Agent, or Firm*—Klima & Pezzlo, P.C.

[57] ABSTRACT

A glaucoma drain implanting device having a body portion including a proximal end and a distal end, a separate nozzle portion connected to the distal end of the body and including a drain delivery passageway, a plunger having a plunger tip movably disposed relative to the drain delivery passageway, and a drain receiver. A method of using the drain implant device includes the steps of advancing a glaucoma drain into the drain delivery passageway of the device, thereby placing the glaucoma drain in a staged configuration, and, placing an exit of the drain delivery passageway proximately to the eye and further advancing the glaucoma drain to cause the glaucoma drain to pass through the exit of the drain delivery passageway and into the tissue of the eye.

19 Claims, 7 Drawing Sheets

GLAUCOMA DRAIN IMPLANTING DEVICE AND METHOD

FIELD OF THE INVENTION

The present invention is directed to surgical implantation devices and, more particularly, to a glaucoma drain implanting device for implanting a glaucoma drain.

BACKGROUND OF THE INVENTION

The healthy eye is filled with a fluid called aqueous humor. The ciliary body, located in the posterior chamber of the eye, produces aqueous humor and the Canal of Schlelmm, which is located at the periphery of the anterior chamber, releases aqueous humor into the trabecular meshwork. When the eye does not function properly to drain aqueous humor, an excess of aqueous humor may become present in the eye and the intraocular pressure may rise. The increased intraocular pressure associated with this excess, also known as glaucoma, is the leading cause of blindness. Glaucoma may be treated by medicine and/or by surgery.

Many procedures for treating glaucoma involve increasing the rate of drainage of aqueous humor from the eye. More particularly, many procedures for treating glaucoma involve implanting, injecting, placing or otherwise introducing a drainage device to the eye to increase the rate of drainage of aqueous humor therefrom. Of the many devices and methods currently used to introduced such a drainage to the eye, none has become universally accepted.

SUMMARY OF THE INVENTION

Accordingly, it is a first object of the present invention to provide an improved glaucoma drain implanting device for implanting a glaucoma drain in an eye.

It is a second object of the present invention to provide a glaucoma drain implanting device which may be used to implant a substantially cylindrically shaped glaucoma drain made entirely of a porous biomaterial.

It is a third object of the present invention to provide a glaucoma drain implanting device which may be configured to implant different glaucoma drains.

It is a fourth object of the present invention to provide a glaucoma drain implanting device which may be provided to the user in a pre-loaded configuration.

It is a fifth object of the present invention to provide a glaucoma drain implanting device which is disposable.

It is a sixth object of the present invention to provide a glaucoma drain implanting device which provides drain position information to the user of the device.

It is a seventh object of the present invention to provide a glaucoma drain implanting device for implanting a glaucoma drain with a body having a proximal end and a distal end, a separate nozzle portion connected to a distal end of the body, the nozzle portion including a drain delivery passageway, and a plunger having a plunger tip movably disposed relative to said drain delivery passageway, the plunger tip associated with a drain receiver.

It is an eighth object of the present invention to provide a method of implanting a glaucoma drain including the steps of moving a plunger tip relative to a drain delivery passageway to cause a glaucoma drain to also move relatively to and partially through a drain delivery passageway thereby staging a glaucoma drain and further advancing the plunger tip to cause the glaucoma drain to pass through an exit of the drain delivery passageway and into the tissue of the eye.

The present invention provides an improved device for implanting a glaucoma drain. A preferred embodiment of the device is provided to the user in a preloaded, ready-to-be-used, and disposable configuration and is particularly well suited to implant a cylindrically shaped glaucoma drain made entirely of a porous biomaterial. Importantly, the device of the present invention may be used to implant many different types of glaucoma drains.

The device includes a body portion having a proximal end and a distal end. The body portion is preferably an elongated tubular member. In general, the body portion is configured to be easily grasped by the hand of a user of the device.

The device also includes a separate nozzle portion which is connected to a distal end of the body. The separate nozzle portion has a drain delivery passageway. Providing a separate nozzle portion with the device allows any number of different nozzle portions to be used, each of which may have a different drain delivery passageway. This allows many different types of glaucoma drains to be implanted with the device.

Other factors, aside from the type of glaucoma drain which is to be implanted with the device, may also affect the selection of the separate nozzle portion which is to be used in a given set of circumstances. For example, two separate nozzle portions may be capable of delivering the same glaucoma drain, however, one may provide a better "feel" to a particular user of the device. Since either separate nozzle portion may be used, the user is easily accommodated by the device of the present invention.

The device also includes a plunger with a plunger tip which is provided to be movably disposed relative to the drain delivery passageway. The plunger tip, which is advanced by the plunger, is provided to advance a glaucoma drain through the drain delivery passageway and into the eye. The plunger may be provided with an engagement member for allowing a user of the device to better control the advancement of the plunger.

The plunger tip which is provided with the plunger is associated with a drain receiver. The purpose of the drain receiver is to properly orient a glaucoma drain for engagement by the plunger tip and/or for advancement through the drain delivery passageway.

The device may be configured to provide drain position information. For example, the body portion and the nozzle portion may be made entirely of a transparent material thus allowing a user of the device to assess drain position by sight.

To use the device, a user grasps the body of the device in one hand and with a finger or fingers of the other end engages the plunger. The user then moves the plunger distally relative to the body of the device to advance the plunger tip into engagement with the glaucoma drain. As the plunger is advanced the glaucoma drain enters the separate nozzle portion drain delivery passageway and is considered to be in a staged configuration.

Then, the device, and in particular, the exit of the drain delivery passageway is brought into close proximity to the site of implantation of the glaucoma drain in the eye. The plunger tip is further advanced causing the drain to pass through the exit of the drain delivery passageway and into to the tissue of the eye to complete the implantation. The device is then moved away from the eye.

Thus, the present invention provides a device that is particularly well suited to implant a substantially cylindrically shaped glaucoma drain made entirely of a porous biomaterial. However, the device, and in particular, the drain receiver, the nozzle portion, and the plunger tip may be configured to implant many different types of glaucoma drains. It is thus possible with the device of the present invention to use a substantially similar method to implant many different types of glaucoma drains. In sum, the device of the present invention provides an improved glaucoma drain device and, in general, an improvement to the art of implanting a glaucoma drain.

DETAILED DESCRIPTION OF THE PREFERRED EMBODIMENT

Figures 1, 2A, 2B, 3, 4:
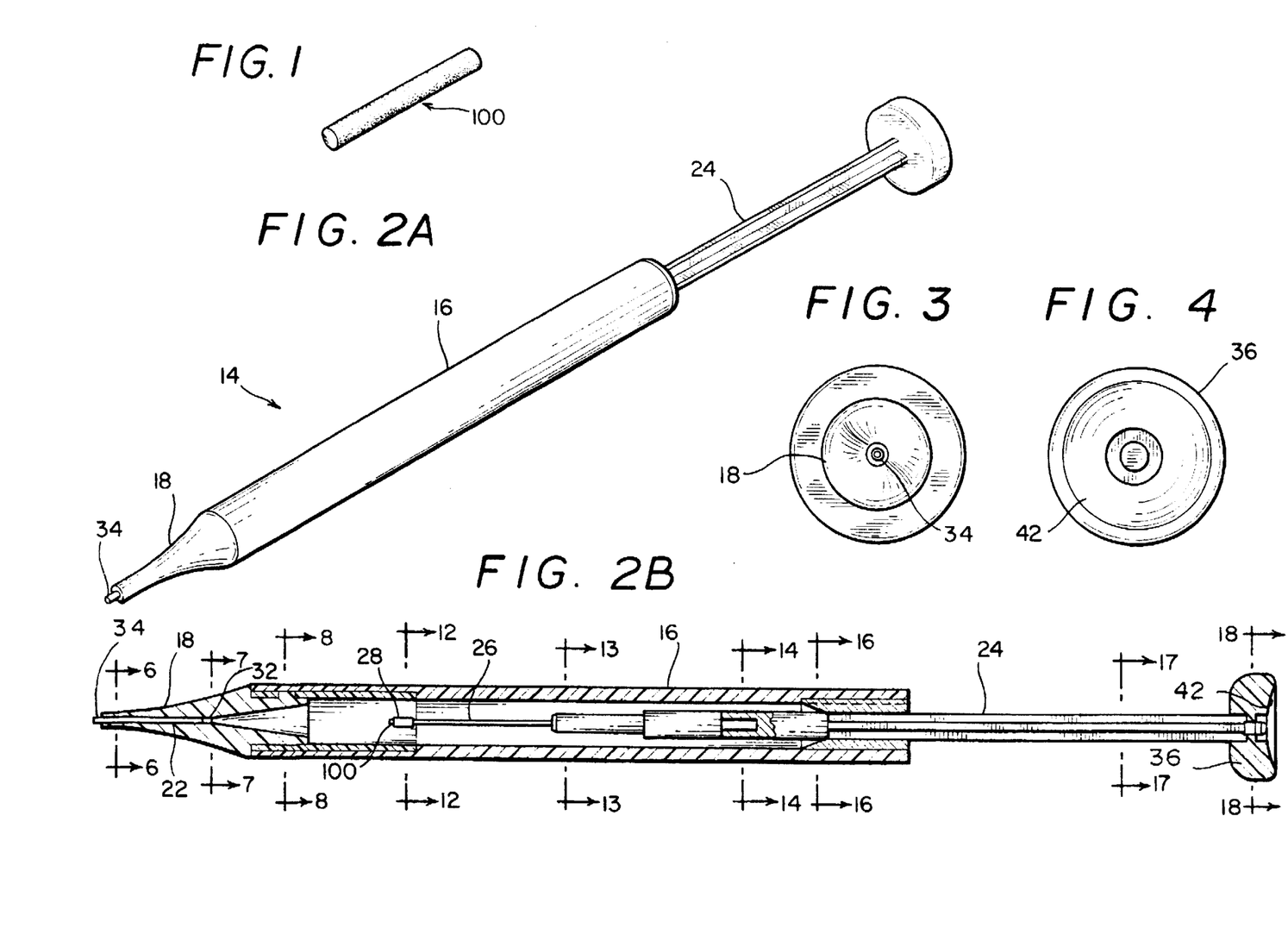
FIG. 1 is a perspective view of a glaucoma drain.
FIG. 2A is a perspective view of a preferred embodiment of a glaucoma drain implanting device according to the present invention loaded with a glaucoma drain.
FIG. 2B is a longitudinal cross-sectional view of the glaucoma drain implanting device shown in FIG. 2A.
FIG. 3 is a distal end view of the glaucoma drain implanting device shown in FIG. 2A.
FIG. 4 is a proximal end view of the glaucoma drain implanting device shown in FIG. 2A.

FIG. 1 is a perspective view of a preferred glaucoma drain 100. The glaucoma drain 100 is preferably, cylindrical shaped, and made preferably of collagen-based cross-linked biopolymer. A preferred collagen-based cross-linked biopolymer for use in the present invention described in U.S. Pat. No. 4,978,352 to Fedorov et al. and entitled "Process For Producing Collagen-Based Cross-Linked Biopolymer, And Implant From Said Biopolymer, Method For Producing Said Implant, And Method For Hermetization Of Cornal Dr. Scleral Wounds Involved In Eye Injuries, Using Said Implant" is incorporated herein by reference.

FIG. 2A shows a perspective view of a glaucoma drain implanting device 14 according to the present invention. The device 14 includes generally, and as shown further in FIG. 2B, a body portion 16, a separate nozzle portion 18 connected to body portion 16 and having a drain delivery passageway 22 with an entrance 32 and an exit 34, and a plunger 24 movably disposed relative to the drain delivery passageway 22 and having a plunger tip 26. The glaucoma drain 100 is disposed within receiver 28 which is preferably made of a material such as silicone tubing.

As shown in FIGS. 2A and 2B, body portion 16 of device 14 is preferably an elongated tubular member. However, as device it is intended to be hand held, body portion 16 may be of any shape or material which is easily grasped.

As shown in the distal end view of FIG. 3, exit 34 of drain delivery passageway 22 is preferably circular and centered about the longitudinal axis of nozzle 18. As shown in FIGS. 1–4, the plunger 24 of device 14 is preferably provided with an engagement member 36 for engagement by a finger or the fingers of a user. Preferably, engagement member 36 is a substantially disk shaped member rotatably connected to a proximal end of plunger 24 and having a concave distal end face 42. Engagement member 36 may include an internally threaded distally extending skirt (not shown) for threaded engagement with a threaded proximal surface on body 16. Alternatively, body portion 16 may include at least one finger engageable protrusion (not shown) cooperative with engagement member 36.

FIG. 3 shows a distal end view of device 14. Exit 34 of drain delivery passageway 22 is preferably circular and centered about the longitudinal axis of nozzle 18.

FIG. 4 shows a proximal end view of device 14. The plunger 24 of device 14 is preferably provided with an engagement member 36 for engagement by a finger or the fingers of a user. As shown in FIGS. 1–14, engagement member 36 is preferably a substantially disk shaped member having a concave distal end face 42 rotatably connected to a proximal end of plunger 24. Engagement member 36 may include an internally threaded distally extending skirt (not shown) for threaded engagement with a threaded proximal surface on body 16. Alternatively, body portion 16 may include at least one finger engageable protrusion (not shown) cooperative with engagement member 36.

Figure 5:
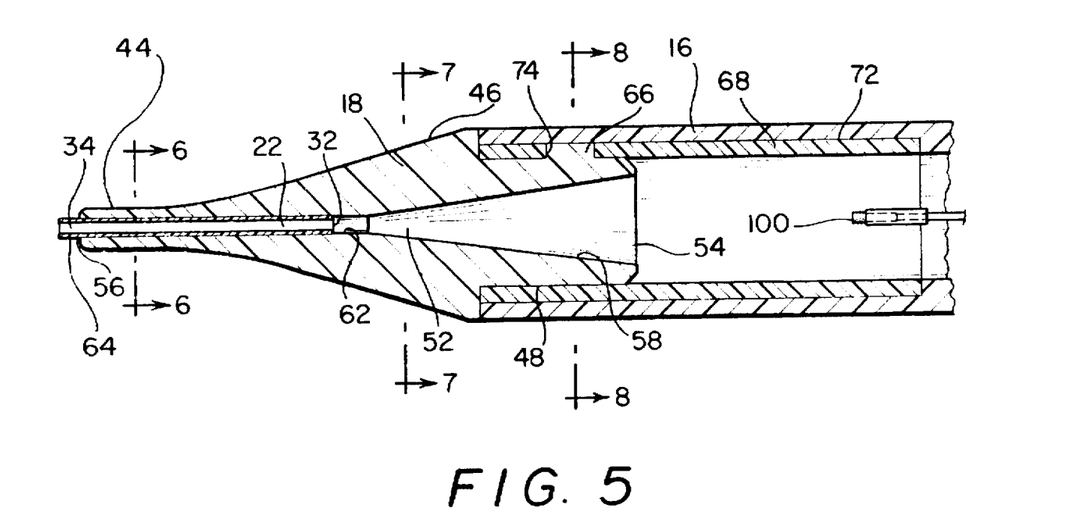
FIG. 5 is a broken away longitudinal cross-sectional view of a distal portion of the glaucoma drain implanting device shown in FIG. 2A.
Figure 6:
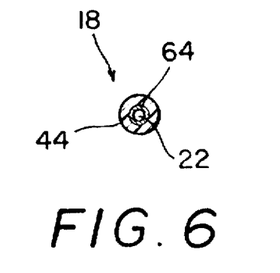
FIG. 6 is a transverse cross-sectional view of the glaucoma drain implanting device shown in FIG. 5 along the line 6—6.
Figure 7:
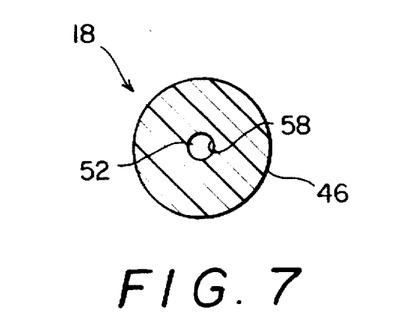
FIG. 7 is a transverse cross-sectional view of the glaucoma drain implanting device shown in FIG. 5 along the line 7—7.
Figure 8:
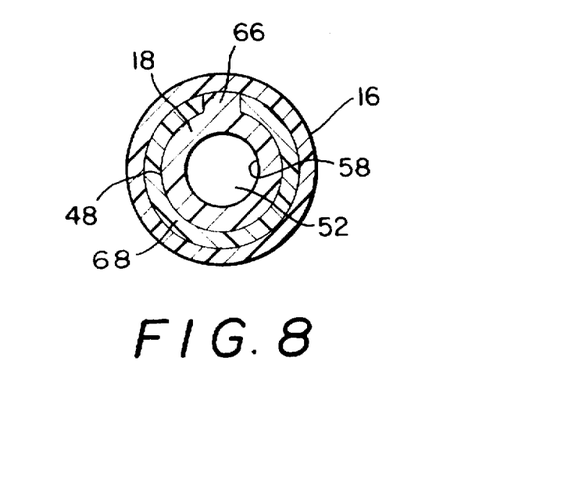
FIG. 8 is a transverse cross-sectional view of the glaucoma drain implanting device shown in FIG. 5 along the line 8—8.

Separate nozzle portion 18 including drain delivery passageway 22 is shown in FIGS. 5–8. Nozzle portion 18 includes a passageway 52 having an entrance 54, a guiding portion 58, a main portion 62, and an exit 56. Preferably, nozzle portion 18 is made of plastic. As shown in FIGS. 5–6, a drain delivery passageway sleeve 64, preferably made of metal, is mounted distally in the main portion 62 of nozzle portion passageway 52. Sleeve 64 defines a drain delivery passageway 22 having a circular transverse cross-sectional area. It is preferable for the distal end of sleeve 64 to extend slightly past the exit 56 of nozzle portion passageway 52 and for the longitudinal axes of passageway 52 and drain delivery passageway 22 to be coincident with the longitudinal axis of body portion 16.

In the preferred embodiment shown in FIGS. 5–8, separate nozzle portion 18 includes a distally extending cylindrical portion 44, a conic middle portion 46, and a proximally extending connecting portion 48. Connecting portion 48 is preferably cylindrical in cross-section and includes a radially protruding tab 66. A nozzle mounting sleeve 68 mounted in a receiving portion 72 of body portion 16 is configured to accept connecting portion 48 and includes a detent 74. When connecting portion 48 is substantially within sleeve 68, tab 66 is engaged and retained by detent 74. Note that this arrangement prevents all movement of separate nozzle portion 18 relative to body portion 16.

Figure 25:
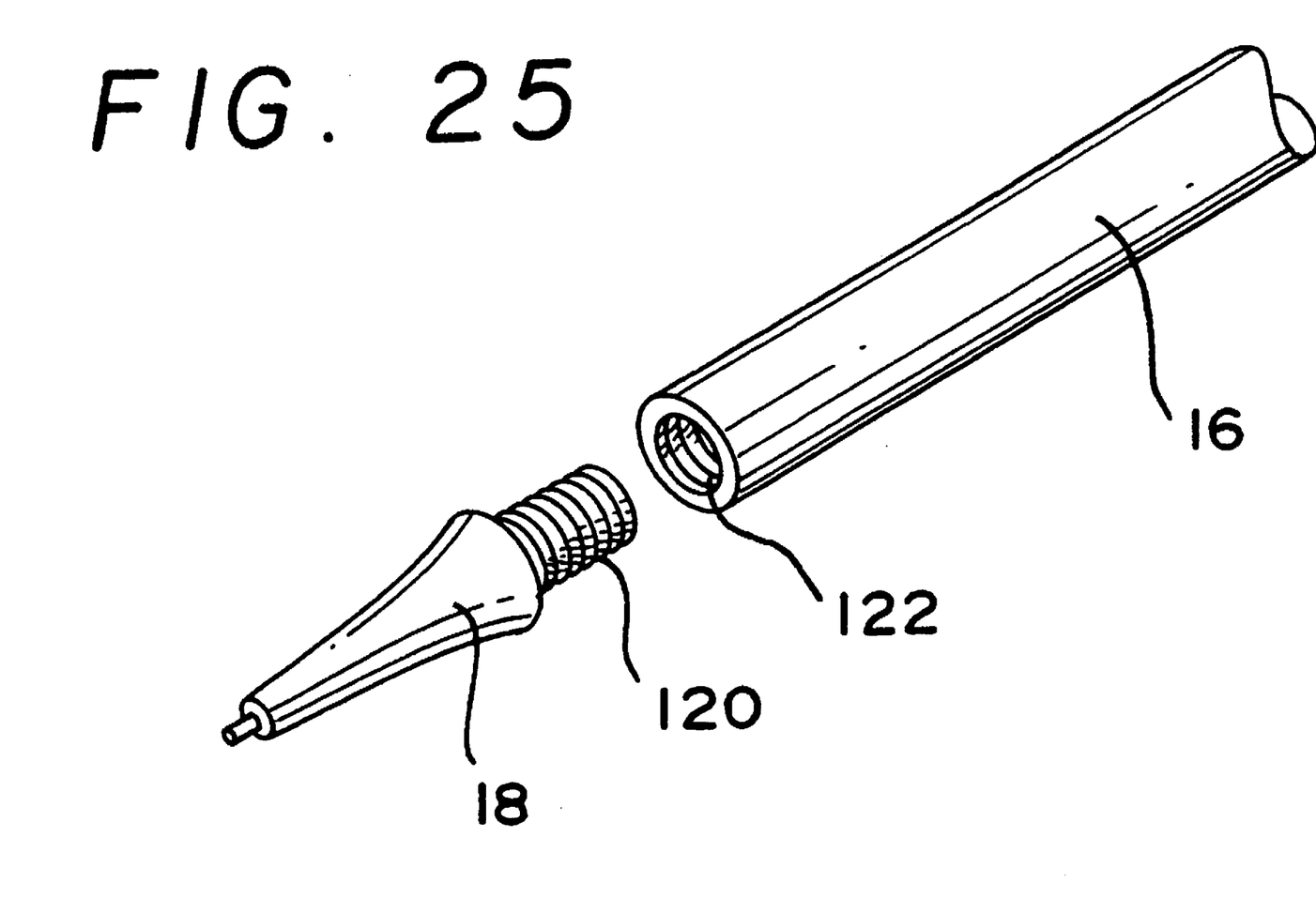
FIG. 25 is a partial perspective view of the nozzle portion and the body portion.

Alternative methods of connecting as shown in FIG. 25 separate nozzle portion 18 to body portion 16 are contemplated. For example, separate nozzle portion 18 may include a threaded portion 120 which engages a corresponding threaded portion 122 on body 16. In another embodiment, separate nozzle portion 18 may connect to body portion 16 in a snap fit type manner e.g. barb and catch configuration.

Alternatively, separate nozzle portion 18 may connect to body portion 16 in such a manner that once nozzle portion 18 is attached to body portion 16 it may not be removed therefrom. Such an embodiment contemplates a device 14 which is provided to a user in a one-time-use disposable configuration. Device 14 may also be provided to a user with many different separate nozzle portions 18 which may be connected and removed according to the particular glaucoma drain 100 to be installed.

The above-described preferred embodiment of separate nozzle portion 18 is particularly well suited for delivering a glaucoma drain 100, shown in FIG. 5, made of a cylindrically-shaped length of porous biomaterial. Note, however, that separate nozzle portion 18 is separate from device 14 so that different nozzles may be connected to body 16 for the delivery of different types of glaucoma drains to the eye.

Figures 9, 10:
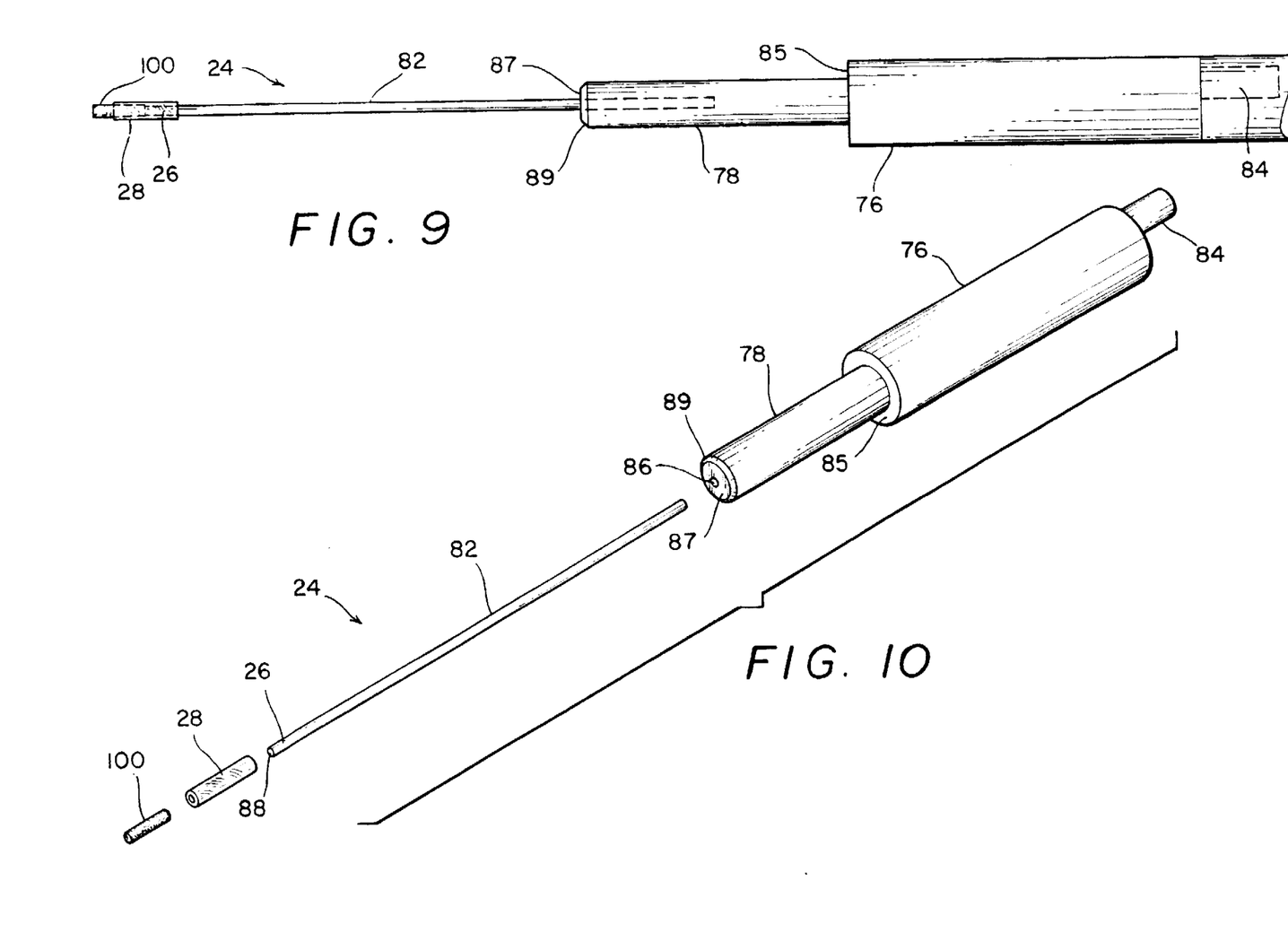
FIG. 9 is a broken away side elevational view of a distal portion of the plunger and the plunger tip with the drain receiver and the glaucoma drain shown in FIG. 2A.
FIG. 10 is an exploded perspective view of the broken away distal portion of the plunger and plunger tip with the drain receiver and the glaucoma drain shown in FIG. 9.

FIGS. 9–10 show a distal portion of a preferred embodiment of plunger 24. The distal portion of plunger 24 includes a cylindrical distal base portion 76 having an axially offset proximally protruding connector 84, a cylindrical middle portion 78 which is integral with base portion 76 and extending axially in a distal direction therefrom, and a substantially rod-shaped axially extending portion 82 mounted in an axial hole 86 in middle portion 78. Connector 84 connects distal base portion 76 to plunger proximal base portion 77.

Note from FIGS. 9–10 that plunger 24, telescopes downwardly in a distal direction. In particular, the distal end of distal base portion 76 includes a first face 85. The distal end of middle portion 78 includes a second face 87 and a chamfer 89. First face 85 and second face 87 may be used as platforms against which a spring (not shown) or other biasing means may provide a force for directing, guiding, or resisting the movement of the plunger 24 relative to body 16.

Figure 11:
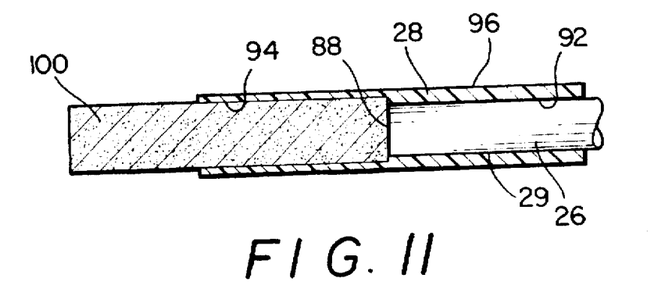
FIG. 11 is a broken away detailed longitudinal cross-sectional view of the plunger tip with the drain receiver and the glaucoma drain shown in FIG. 9.

As shown in FIGS. 9–10 and in detail in FIG. 11, a plunger tip 26 is included with plunger 24. Plunger tip 26 is located at and is preferably integral with the distal end of extending portion 82 of plunger 24. The plunger tip 26 of the preferred embodiment includes a substantially flat end face 88 for engaging a substantially cylindrically shaped glaucoma drain 100 made entirely of a porous biomaterial.

Plunger tip 26 may have any configuration necessary to engage a glaucoma drain 100. For example, the distal end of plunger tip 26 may taper distally to a point. Further, plunger tip 26 may include an end face 88 which is any shape, such as concave or convex, or any texture, such as ridged or bumped. As another example, plunger tip 26 may have any number of members projecting distally therefrom for engaging a glaucoma drain 100.

To provide for the delivery of different types of glaucoma drains with the device of the present invention, the provision of interchangeable plunger tips 26 with device 14 is contemplated. For example, plunger tip 26 may be removable from plunger extending portion 82. Alternatively, plunger tip 26 may be integral with plunger extending portion 82 and the proximal end of plunger extending portion 82 may be threaded for threaded engagement with axial hole 86.

Associated with plunger tip 26 is a drain receiver 28 shown in FIG. 11. Preferably, drain receiver 28 is a substantially elastic tubular member having a first inner diameter 92 defining a plunger tip engaging portion and a second inner diameter 94 defining a drain engaging portion. In the preferred embodiment shown, first inner diameter 92 is larger than second inner diameter 94 and further, a plunger passageway 29 extends through drain receiver 28.

Note that drain receiver 28 is independent of plunger tip 26. Also note, however, that drain receiver 28 may be integral with the distal end of plunger tip 26. For example, drain receiver may be a recess in end face 88 of plunger tip 26.

Alternatively, drain receiver 28 may be integral with separate nozzle portion 18. For example, separate nozzle portion passageway 52 may include a drain receiving portion. Any drain receiver 28 in which a glaucoma drain may be received according to the present invention must be configured to properly orient a glaucoma drain for engagement by the plunger tip and/or for advancement thereof through the drain delivery passageway. Most importantly, the device 14, and in particular, drain receiver 28, nozzle portion 18, and plunger tip 26 may be configured to deliver many different types of glaucoma drains to the eye.

Figure 12:
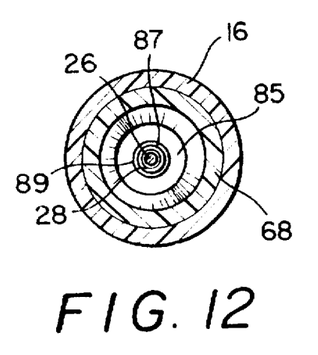
FIG. 12 is a transverse cross-sectional view of the glaucoma drain implanting device shown in FIG. 2B along the line 12—12.

In FIG. 12, a transverse cross-sectional view of device 14 along the line 12–12 in FIG. 1 is shown. Concentrically arranged about plunger tip 26 are drain receiver 28, nozzle mounting sleeve 68 and body 16. Second face 87, chamfer 89 and first face 85 may also be appreciated in FIG. 12.

Figure 13:
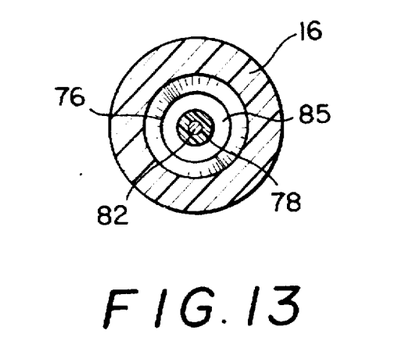
FIG. 13 is a transverse cross-sectional view of the glaucoma drain implanting device shown in FIG. 2B along the line 13—13.

FIG. 13 shows a transverse cross-sectional view of device 14 along the line 13–13 in FIG. 2. Plunger extending portion 82 is shown axially mounted in plunger middle portion 78. Stop face 85 separates integral middle and distal base portions, 78 and 76, respectively.

Figure 14:
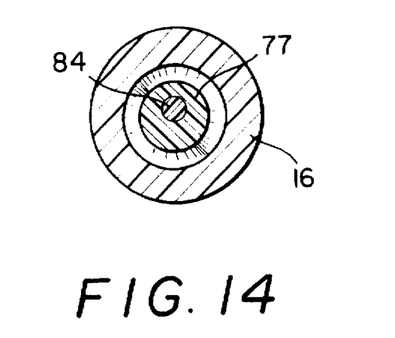
FIG. 14 is a transverse cross-sectional view of the glaucoma drain implanting device shown in FIG. 2B along the line 14—14.

A transverse cross-sectional view of device 14 along the line 14–14 in FIG. 2 is shown in FIG. 14. Distal base portion 76 and proximal base portion 77 are connected by way of axially offset connector 84 which is shown within proximal base portion 77.

FIGS. 15–18 show a proximal portion of device 14 including a proximal portion of plunger 24. A plunger proximal base portion 77 is preferably integral with a control portion 98 which extends proximally and axially from proximal base portion 77 and has a substantially cross-shaped transverse cross-sectional profile. An engagement member 36 is rotatably connected to the proximal end of plunger control portion 98.

Figure 15:
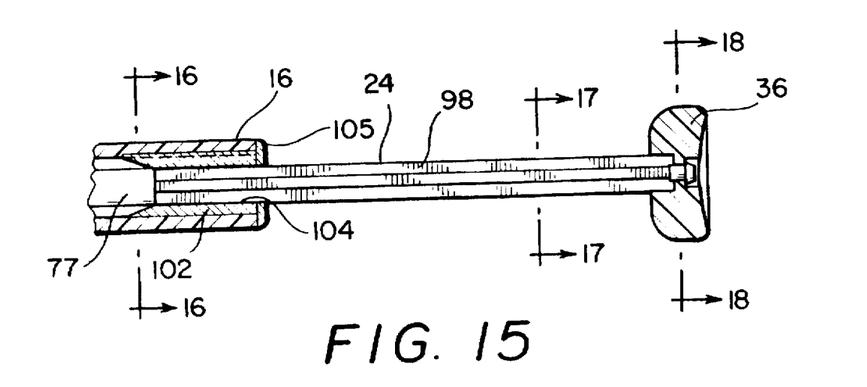
FIG. 15 is a proximal broken away longitudinal cross-sectional view of the glaucoma drain implanting device shown in FIG. 2B.
Figure 16:
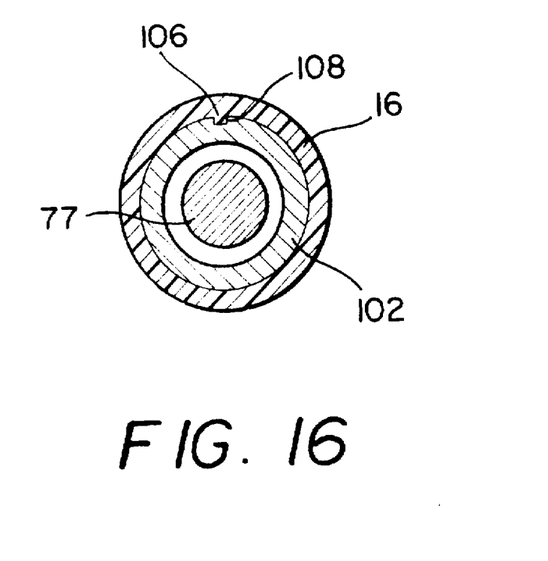
FIG. 16 is a transverse cross-sectional view of the glaucoma drain implanting device shown in FIG. 15 along the line 16—16.

As shown in FIG. 15 and in the transverse cross-sectional view of FIG. 16, a guide member 102 is preferably mounted within the proximal end of body 16. A key 106 and keyway 108 are provided on body 16 and guide member 102, respectively for improving the connection therebetween. As is further shown in FIG. 15, an endcap 105 may also be used to further secure guide member 102 to body 16. Guide member 102 includes a guideway 104, which extends axially therethrough and has a substantially cross-shaped transverse cross-sectional profile for slidably supporting plunger 24, along control portion 98. Note that the substantially cross-shaped transverse cross-sectional profile of the plunger control portion 98 and guideway 94 prevent the plunger 24 from rotating relative to the longitudinal axis of body 16.

Axial displacement of the plunger 24 relative to the body 16 is limited in the proximal direction by proximal base portion 77. Axial displacement of the plunger 24 relative to the body 16 is limited in the distal direction by engagement member 36.

Figure 17:
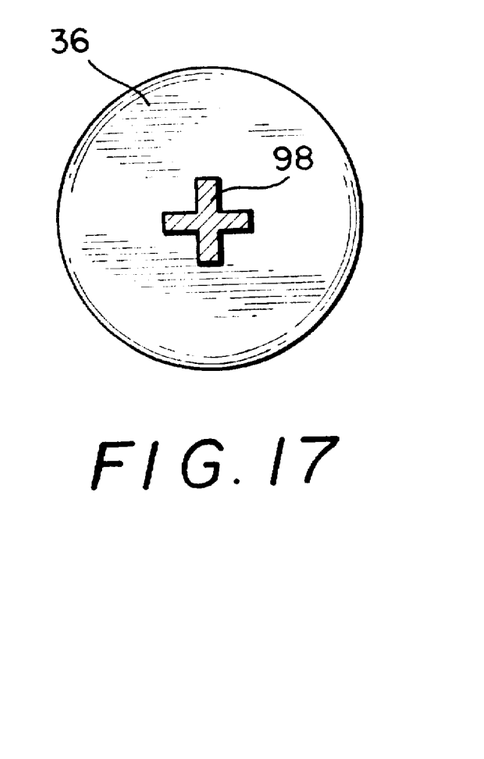
FIG. 17 is a transverse cross-sectional view of the glaucoma drain implanting device shown in FIG. 15 along the line 17—17.
Figure 18:
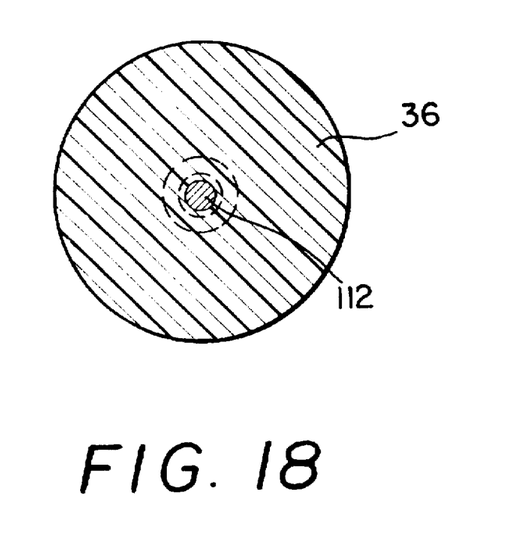
FIG. 18 is a transverse cross-sectional view of the glaucoma drain implanting device shown in FIG. 15 along the line 18—18.

The cross-shaped transverse cross-sectional profile of the plunger control portion 98 and the distal side of engagement member 36 are clearly viewable in the transverse cross-sectional view of FIG. 17. In FIGS. 15 and 18, the engagement member 36 is shown rotatably connected to the control portion 98 of plunger 24, by a barb 112.

Figure 19:
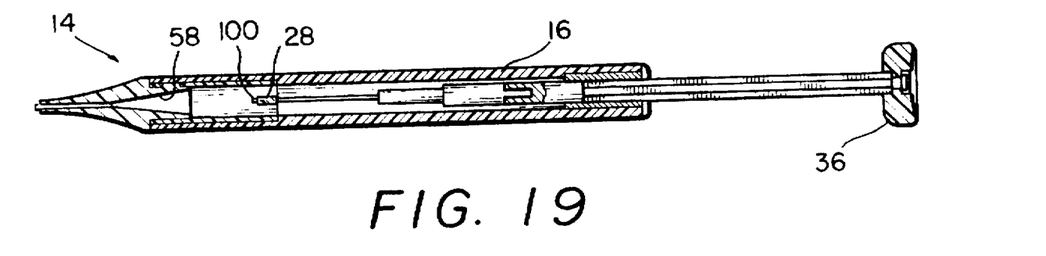
FIG. 19 is a longitudinal cross-sectional view of the glaucoma drain implanting device in the loaded configuration shown in FIG. 2B.
Figure 20:
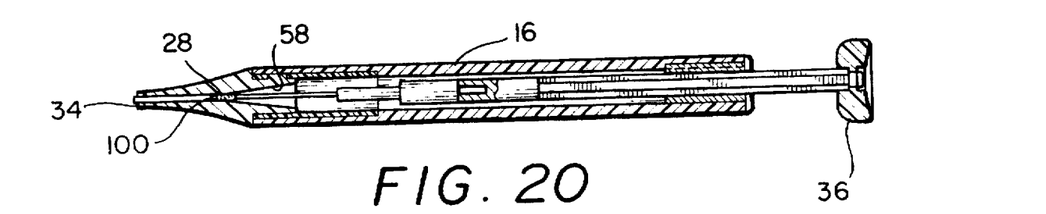
FIG. 20 is a longitudinal cross-sectional view of the glaucoma drain implanting device shown in FIG. 19 with the loaded glaucoma drain partially advanced.

The device 14 is preferably provided to a user in the loaded and ready-to-be-used configuration shown in FIG. 19. To implant a cylindrically shaped glaucoma drain 100 made entirely of a porous biomaterial with the above described preferred embodiment of device 14 according to the present invention, a user grasps the body 16 of device 14 with one hand and with a finger or fingers of the other hand engages engagement member 36. The user pushes on engagement member 36 to displace plunger 24, plunger tip 26, drain receiver 28 and glaucoma drain 100 distally with respect to the body 16. Nozzle passageway guiding portion 58 guides glaucoma drain 100, drain receiver 28 and plunger tip 26 into nozzle portion passageway main portion 62 as shown in FIG. 21.

Figure 21:
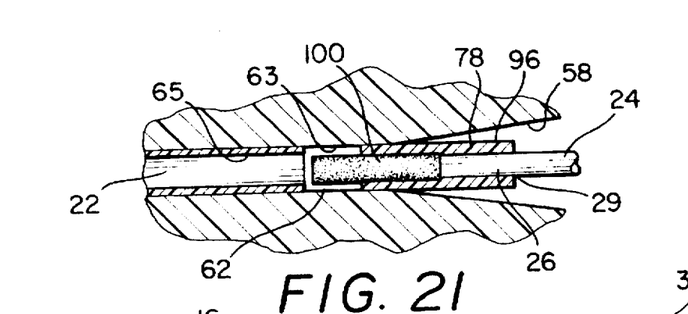
FIG. 21 is a detailed broken away longitudinal cross-sectional view of the drain engaging tip with the drain receiver and glaucoma drain shown in FIG. 20.

Importantly, and as shown in FIG. 21, drain receiver outer diameter 96 is smaller than nozzle portion passageway main portion diameter 63 but larger than drain delivery passageway valve inner diameter 65. Therefore, as the plunger 24 is further advanced, glaucoma drain 100 enters drain delivery passageway 22 but drain receiver 28 abuts the proximal end of drain delivery passageway sleeve 65 thereby causing glaucoma drain 100 to disengage from drain receiver 28.

Figure 24:
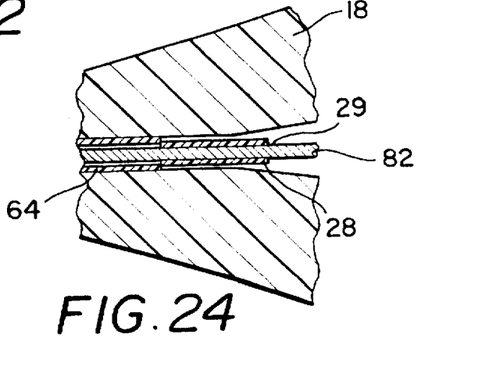
FIG. 24 is a detailed broken away longitudinal cross-sectional view of a mid-portion of the nozzle, the drain delivery passageway, the plunger, and the drain receiver shown in FIG. 22.

Further advancement of the plunger 24 causes plunger tip 26 to slide through drain receiver plunger passageway 29 and into drain delivery passageway 22. As shown in FIG. 24, drain receiver 28 remains stationary relative to body 16 as plunger extending portion 82 slides therethrough. When the plunger tip 26 enters the drain delivery passageway 22, the glaucoma drain 100 is considered to be in a staged configuration.

Figure 22:
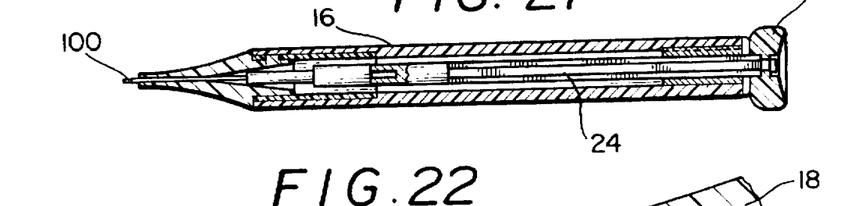
FIG. 22 is a longitudinal cross-sectional view of the glaucoma drain implanting device shown in FIG. 19 with the loaded glaucoma drain fully advanced.
Figure 23:
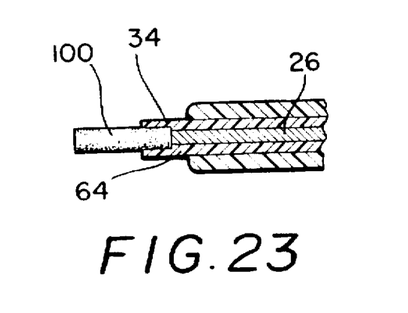
FIG. 23 is a detailed broken away longitudinal cross-sectional view of a distal portion of the nozzle, the drain delivery passageway, the plunger tip, and the glaucoma drain shown in FIG. 22.

The device 14 is then brought into close proximity to the eye. As the plunger tip 26 is advanced further, the glaucoma drain 100 is caused to pass through exit 34 into the tissue of the eye. As shown in FIGS. 22–24, insertion is completed when the distal end of plunger tip 26 is flush with exit 34. Preferably, and as shown in FIGS. 22 and 23, plunger tip 26 is prevented from extending past exit 34 by contact of engagement member 36 with the proximal end of body 16. The device 14 is then moved away from the eye. Other embodiments of the device 14 which are used to implant the same or different glaucoma drains 100 are operated similarly.

In order to aid in the implantation of a glaucoma drain 100 into the eye, device 14 may be configured to provide drain position information to a user thereof. For example, body portion 16 and nozzle portion 18 may be made of a transparent material thereby allowing a user of device 14 to assess drain position by sight. As another example, plunger 24 may be provided with lines of demarcation indicative of the extent to which plunger tip 26 has advanced through drain delivery passageway 22. As another example, drain delivery passageway 22 and drain receiver 26 may be configured to provide different impediments to the advancement of a glaucoma drain 100 thereby providing drain position information to the user of the device in the form of a perceptible change in the force required to advance the glaucoma drain. For example, the coefficient of friction associated with advancement of glaucoma drain 100 through drain delivery passageway 22 may be different than the coefficient of friction associated with the disengagement of glaucoma drain 100 from drain receiver 28.

What is claimed is:

1. A glaucoma drain device, said device comprising:
   a body portion having a proximal end and a distal end;
   a separate nozzle portion connected to a distal end of said body, said nozzle portion including a glaucoma drain delivery passageway;
   a plunger having a plunger tip movably disposed relative to said glaucoma drain delivery passageway;
   a glaucoma drain; and,
   a glaucoma drain receiver comprising a sleeve, said plunger tip inserted in one end of said sleeve and said glaucoma drain insert in another end of said sleeve.

2. A device according to claim 1, wherein said drain receiver is defined by a substantially elastic tubular member having a first diameter defining a plunger tip engaging portion, a second diameter defining a glaucoma drain engaging portion, and a longitudinal passageway.

3. A device according to claim 1, wherein said drain receiver is defined by a drain receiving portion in said nozzle portion.

4. A device according to claim 1, wherein said nozzle portion passageway includes a guiding portion for guiding said plunger tip into said drain delivery passageway.

5. A device according to claim 4, wherein said guiding passageway portion of said nozzle portion passageway is defined by an inwardly tapering passageway portion.

6. A device according to claim 1, wherein said nozzle portion includes a distally extending portion having a radially protruding tab and said distal end of said body portion includes a receiving portion in which a nozzle mounting sleeve is mounted, said nozzle mounting sleeve including a detent for retaining said tab on said distally extending portion of said nozzle portion.

7. A device according to claim 1, wherein said nozzle portion snap fits into said distal end of said body portion for connecting said nozzle portion to said body portion.

8. A device according to claim 1, wherein said distally extending portion of said nozzle portion is threaded for threaded engagement with a corresponding threaded surface on said body portion.

9. A device according to claim 1, wherein said nozzle portion includes a passageway in which a metal sleeve is mounted said metal sleeve defining said drain delivery passageway.

10. A device according to claim 1, wherein said body portion includes a guide member having a guideway for guiding said plunger relative to said body portion.

11. A device according to claim 10, wherein said guide member is configured to prevent axial rotation of said plunger relative to said body portion.

12. A device according to claim 1, wherein a distal portion of said plunger defines a substantially telescopic shape.

13. A device according to claim 1, wherein a biasing device is disposed between said plunger and said body portion for biasing movement of said plunger relative to said body portion.

14. A device according to claim 1, wherein said glaucoma drain is preloaded in said drain receiver.

15. A device according to claim 1, wherein said nozzle portion and said body portion are made of a transparent material.

16. A device according to claim 15, wherein said material is plastic.

17. A device according to claim 1, wherein said nozzle portion and said body portion are made of metal.

18. A device according to claim 1, wherein said glaucoma drain is made of a collagen based copolymer.

19. A device according to claim 1, wherein said plunger includes lines of demarcation indicative of the position of said glaucoma drain in said drain delivery passageway.

* * * * *